(12) United States Patent
Lei et al.

(10) Patent No.: US 6,777,445 B2
(45) Date of Patent: Aug. 17, 2004

(54) FULLERENE PHARMACEUTICAL COMPOSITIONS FOR PREVENTING OR TREATING DISORDERS

(75) Inventors: Huan-Yao Lei, Taipei (TW); Chen-Kung Chou, Taipei (TW); Tien-Yau Luh, Taipei (TW)

(73) Assignee: National Health Research Institute, Taipei (TW)

( * ) Notice: Subject to any disclaimer, the term of this patent is extended or adjusted under 35 U.S.C. 154(b) by 10 days.

(21) Appl. No.: 09/981,951

(22) Filed: Oct. 17, 2001

(65) Prior Publication Data

US 2002/0098180 A1 Jul. 25, 2002

Related U.S. Application Data

(63) Continuation of application No. 09/645,682, filed on Aug. 24, 2000, now abandoned.

(30) Foreign Application Priority Data

Mar. 24, 2000 (TW) .......................................... 89105485 A

(51) Int. Cl.$^7$ ............................................... A61K 31/19
(52) U.S. Cl. ......................... 514/557; 514/553; 514/75; 514/80
(58) Field of Search ........................... 514/75, 80, 553, 514/557

(56) References Cited

U.S. PATENT DOCUMENTS

| | | | | |
|---|---|---|---|---|
| 5,475,172 A | * | 12/1995 | Cahill et al. | .................. 585/27 |
| 5,587,476 A | * | 12/1996 | Kampe et al. | .............. 540/472 |
| 5,648,523 A | * | 7/1997 | Chiang | ........................ 562/100 |
| 5,994,410 A | * | 11/1999 | Chiang et al. | .............. 514/709 |
| 6,162,926 A | * | 12/2000 | Murphy et al. | ............. 548/417 |

OTHER PUBLICATIONS

Jensen et al, Bioorganic & Medicinal Chemistry, vol. 4(6), pp. 767–779, 1996.*
Lin et al, Virology, vol. 275, pp. 258–262, 2000.*
Wang et al, J. Med. Chem., vol. 42, pp. 4614–4620, 1999.*

* cited by examiner

*Primary Examiner*—James H. Reamer
(74) *Attorney, Agent, or Firm*—Sonnenschein, Nath & Rosenthal

(57) ABSTRACT

The present invention relates to a method for treating a disease, comprising administering a therapeutically effective amount of a pharmaceutical composition comprising a fullerene. The diseases treated comprise bacterial and viral diseases such as those cause by Gram positive and Gram negative bacteria, Dengue 2 virus and viral encephalitis. The fullerene is administered in vivo in an amount of about 0.001 to about 100 mg/kg of body weight of the subject.

23 Claims, 10 Drawing Sheets

FIG. 7

| TREATMENT (IN VITRO CULTURE 4 H) | BACTERICIDAL ASSY OF GROUP A STREPTOCOCCI (CFU/ML) |
|---|---|
|  | $(3.2 \pm 1.1) \times 10^8$ |
| C60 5 UG/ML | $(3.8 \pm 2.1) \times 10^8$ |
| C60 50 UG/ML | $(1.1 \pm 1.0) \times 10^8$ |
| C60 500 UG/ML | $(8.5 \pm 2.1) \times 10^6$ |

FULLERENE PHARMACEUTICAL COMPOSITIONS FOR PREVENTING OR TREATING DISORDERS

This application is a continuation of Ser. No. 09/645,682 filed Aug. 24, 2000 now abandoned.

RELATED APPLICATION DATA

This Application claims priority under 35 U.S.C. §119 to Taiwanese (ROC) Application No. 089105485, filed Mar. 24, 2000, now Taiwanese (ROC) Patent No. 09011012000.

1. Field of the Invention

The present invention relates to the use of fullerenes in preventing or treating disorders, particularly infections.

2. Background of the Invention

Fullerenes are formed when vaporized carbon condenses in an inert gas atmosphere. Fullerenes are a class of carbon molecule having an even number of carbon atoms arranged in the form of a cluster, such as a closed hollow cage, typically spheroid like a soccer ball, wherein the carbon-carbon bonds define a polyhedral structure. The carbon clusters contain an even amount of carbon atoms, generally ranging from 40–80 carbon atoms. Typically, fullerenes each have 12 pentagons, but differing numbers of hexagons. This is in accordance with Euler's law that states that for any polygon with n edges, where n is an even number greater than 22, at least one polyhedron can be constructed with 12 pentagons and (n−20)/2 hexagons. The pentagons are required in order to allow curvature and eventual closure of the surface upon itself. The majority of the fullerenes produced are $C_{60}$ and $C_{70}$. The most abundant species to date is the $C_{60}$ molecule known as buckminsterfullerene, named after R. Buckminster Fuller, the architect of the geodesic dome. Its crystal and molecular structure have been resolved using single-crystal x-ray diffraction methods (S. Uu, et al., Science, 254:408–410, 1991). $C_{60}$ consists of 12 pentagons and 20 hexagons and is classified as an icosahedron, the highest symmetry structure possible.

Several functionalized fullerene derivatives have been reported. For example, fullerenes with relatively small functional groups or addends such as amido, alkoxy, and halides have been described. Macromolecules have also been reported to attach fullerenes.

Fullerenes containing multiple covalently attached substituents or multiple covalently attached amine-derived substituents (A. Hirsch, et al., Angew. Chem. Int. Ed. Engl., 30:1309–1310, 1991; V. Mehrotra, et al., Chem. Mat., 4:20–22, 1992) have been shown to have water solubility, but the lability of the former, and the configurational dynamism and complex isomerism of the latter compound would preclude a ready and unequivocal evaluation of structure-activity data in biological systems. Polyhydroxylated, water-soluble fullerenes have also been prepared, but no single, fully characterized isomer has been isolated to date (L. Y. Chiang, et al., J. Chem. Soc. Chem. Commun., 1992:1701–1793, 1992).

There are several studies on the biological activities of fullerene derivatives (Da Ros, T. et al., Chem. Commun. 1999:663). The size, hydrophobicity, and electronic effects of fullerenes make these molecules particularly attractive for biomedical investigations. Functionalized fullerenes can be used in photodynamic therapy (Tokuyama, H., et al., J. Am. Chem. Soc., 115:7918); as inhibitors of HIV-1 protease (Friedman, S. H. et al., J. Am. Chem. Soc., 115:6505; Sijbesma, R. et al., J. Am. Chem. Soc., 115:6510); as neuroprotective agents (Dugan L. L. et al., Proc. Natl. Acad. Sci. USA 94:9434–9439); as antiapoptotic agents (Hsu S. C. et al., Blood 91:2658–2663; Huang, Y. L. et al., Eur. J. Biochem. 254:38–43); as a protective agent against iron-induced oxidative stress (Lin, A. M. et al., J. Neurochem. 72:1634–1640); or as an in vitro antibacterial agent (Da Ros, T. et al., J. Org. Chem., 1996, 61:9070). However, none of these teach the administration to mammalian subjects of water soluble fullerene derivatives to treat certain bacterial infections, such as E. coli., Staphylococcus aureus, Group A Streptococcus, Group B Streptococcus, vancomycin-resistant Enterococcus infections or bacterial meningitis. Nor do these teach the use of such fullerene compounds to treat viral infections, such as infections caused by dengue 2 virus or Japanese encephalitis virus.

Additionally, current therapies for the above-mentioned infections have numerous disadvantages, such as toxicity and poor efficacy. Therefore, there is a definite need for additional pharmacotherapies to treat these diseases.

SUMMARY OF THE INVENTION

The foregoing problems are solved and a technical advance is achieved in the present invention. The present invention generally comprises the in vivo administration of fullerenes to treat a variety of diseases.

Other features or advantages of the present invention will be apparent from the following detailed description of several embodiments of the invention and from the claims.

BRIEF DESCRIPTION OF THE DRAWINGS

FIG. 7 are graphs showing the results of the plaque reduction neutralization test.

DETAILED DESCRIPTION OF THE INVENTION

Figure 1:
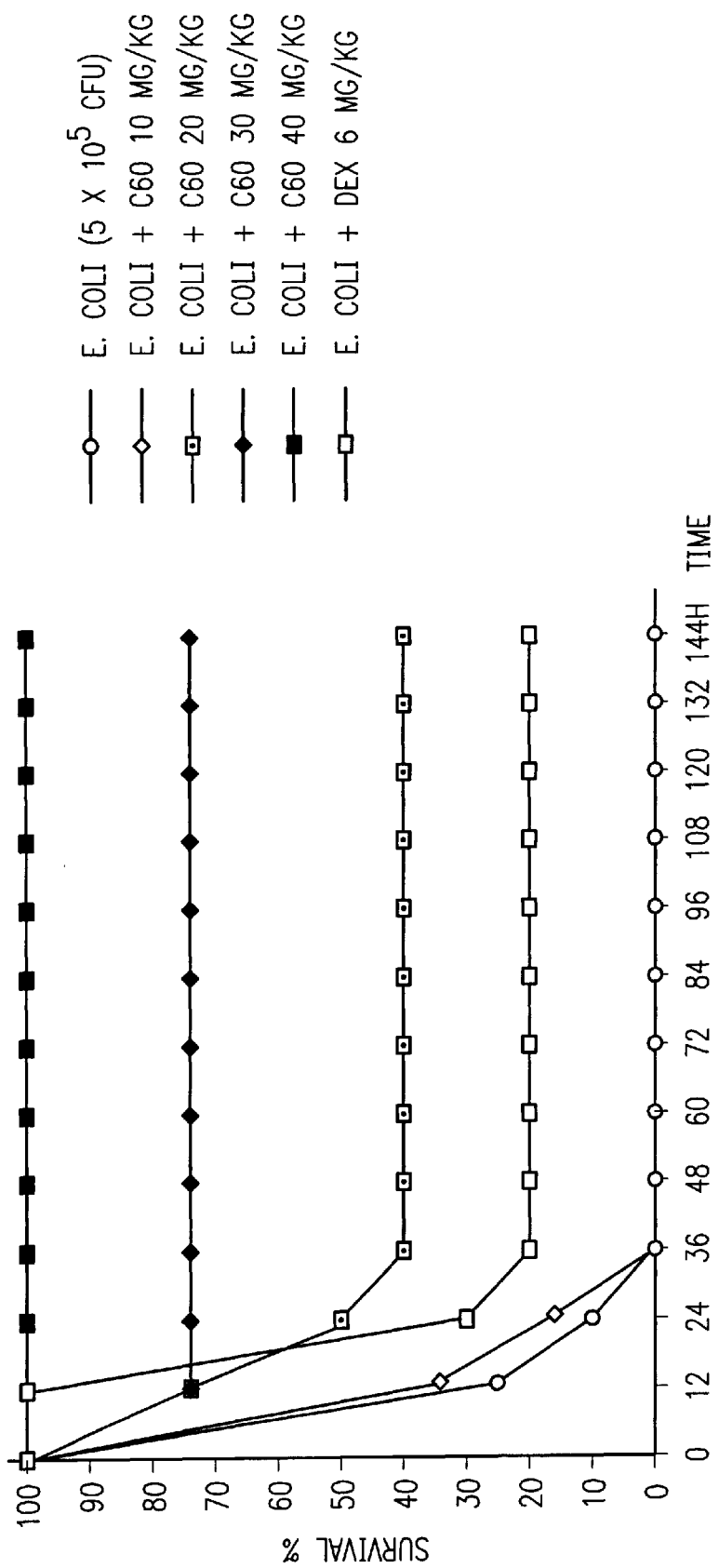
FIG. 1 is a graph showing the effect of a fullerene on E. coli infected mice.

While the present invention may be embodied in many different forms, several specific embodiments are discussed herein with the understanding that the present disclosure is to be considered only as an exemplification of the principles of the invention, and it is not intended to limit the invention to the embodiments illustrated.

When the terms as used herein are referred to, the terms are defined as follows. Any undefined terms have the definitions recognized by persons skilled in the art.

The term "bacterial or viral infections" as used herein generally refers to the disorders (such as inflammation) induced by bacteria or viruses, and the treated physiological alteration or conditions including cytokine production, leukocyte infiltration and cell-increased permeability. The disorders associated with bacterial infection refer to those induced by bacteria, including, but are not limited to, Gram-negative bacteria, particularly E. coli, and Gram-positive bacteria, and Staphylococcus aureus, Group A Streptococcus, Group B Streptococcus or vancomycin-resistant Enterococcus. The disorders associated with viral infection refer to those induced by viruses including, but not limited to, dengue 2 virus and Japanese encephalitis virus.

The term "pharmaceutically acceptable carrier" as used herein generally refers to organic or inorganic materials, which cannot react with active ingredients. The carriers include but are not limited to sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oil, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations. Wetting agents and lubricants such as sodium lauryl sulfate, as well as coloring agents, flavoring agents, lubricants, excipients, tabletting agents, stabilizers, antioxidants and preservatives, can also be present.

The term "therapeutically effective amount" as used herein generally refers to an amount of an agent, for example the amount of a compound as an active ingredient, that is sufficient to effect treatment as defined herein when administered to a subject in need of such treatment. A therapeutically effective amount of a compound, salt, derivative, isomer or enantiomer of the present invention will depend upon a number of factors including, for example, the age and weight of the subject, the precise condition requiring treatment and its severity, the nature of the formulation, and the route of administration, and will ultimately be at the discretion of the attendant physician or veterinarian. However, an effective amount of a compound of the present invention for the treatment of disorders associated with bacterial or viral infection, in particular bacterial meningitis, will generally be in the range of about 10 to about 40 mg/kg body weight of recipient (mammal) per day and more usually about 40 mg/kg body weight per day. Thus, for a 70 kg adult subject, the actual amount per day would typically be about 2,800 mg, and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

The term "treatment" as used herein refers to any treatment of a condition or disease in an animal, particularly a mammal, more particularly a human, and includes:

preventing the disease or condition from occurring in a subject which may be predisposed to the disease but has not yet been diagnosed as having it;

inhibiting the disease or condition, i.e. arresting its development;

relieving the disease or condition, i.e. causing regression of the condition; or relieving the conditions caused by the disease, i.e. symptoms of the disease.

The term "water-soluble fullerene derivative" as used herein generally means any fullerene derivative having an enhanced or improved water solubility including, but not limited to, one or more (a mixture) of a water soluble fullerene derivative(s), in neutral form or a salt form, a single enantiomer or isomer or other derivative or an alkaline salt of an enantiomer of the same.

According to the claimed invention, the water-soluble fullerene derivatives are useful in treating bacterial or viral infections. The use includes but is not limited to the related physiological alteration or conditions inhibiting cytokine (such as tumor necrosis factor-alpha (TNF-alpha) or interleukins (IL)) production, decreasing leukocyte(such as neutrophils) infiltration and reducing leukocyte-induced increased permeability of the blood brain barrier (BBB).

In an embodiment of the invention, a method for treating bacterial meningitis is provided. The pathophysiology of bacterial meningitis involves the invasion and multiplication of bacteria in the subarachnoidal space of the central nervous system (CNS). The bacterium itself, or its degraded products, stimulate the production and release of proinflammatory mediators such a cytokines and prostaglandins by leukocytes, endothelial cells, astrocytes, microglial cells, and other cells in the CNS, and these subsequently lead to an increase in the permeability of the BBB. This triggers transendothelial migration of neutrophils and leakage of plasma proteins that further damage the brain (Benveniste, E. N. Am. J. Physiol. 263:C1–C16 and Perry, V. H., et al., Mol. Med. Today 3:335341). Proinflammatory cytokines have been shown to play a critical role in the pathogenesis of bacterial meningitis. Both TNF-alpha and interleukin-1 (IL-1) were detected in the cerebrospinal fluid of some patients with bacterial meningitis and in experimental animals (Kim, K. S., et al., Exp. Neurol. 145:253–257; Liest, T. P., et al., J. Exp. Med. 167:1743–1748; Lopez-Cortes et al., Clin. Infect. Dis. 16:534–539; Mustafa, M. M. et al., Pediatr. Infect. Dis. J. 8:907–908 and Sharief, M. K., et al., J. Infect. Dis. 166:350–358). Therefore, if an agent has the efficacy of inhibiting the production of TNF-alpha and IL-1, the agent can be used in treating bacterial meningitis. The use in the treatment of bacterial meningitis has been demonstrated in the examples herein. The bacteria include Gram-positive and negative bacteria, such as E. coli, staphylococcus aureus, Group A Streptococcus, Group B Streptococcus or vancomycin-resistant Enterococcus.

Another embodiment of the invention provides a method for treating the disorders induced by a virus, such as dengue 2 virus or Japanese encephalitis virus, which has also been demonstrated in the examples.

Accordingly, the use of fullerenes to treat a disease is disclosed. The invention contemplates the use of any fullerene, including, but not limited to, a buckminsterfullerene or fullerenol. All fullerenes and fullerene derivatives, isomers, salts and enantiomers are referred to herein as "fullerene." In one embodiment of the invention, a water-soluble fullerene derivative is of the Formula I as follows:

$$F[C-X(Y)_n]_m \qquad (I)$$

wherein
- C is carbon attached to two vicinal carbon atoms of the fullerene skeleton at the [6,6] ring junction and form a fused cyclopropane ring;
- F is a fullerene core;
- X and Y are identical or different, and are independently selected from the group consisting of —CO$_2$H, —SO$_3$H and —PO$_3$H;
- n is 0 or 1; and
- m is 1–10.

The preparation of the compounds of Formula I has been disclosed in Dugan, L. L., et al., *Proc. Natl. Acad. Sci. USA* 94:9434–9439, which is incorporated herein by reference.

According to the invention, another embodiment of the water-soluble fullerene derivative is of the Formula II as follows:

$$F(N-Z)_m \quad\quad (II)$$

wherein
- N is attached to two vicinal carbon atoms of the fullerene skeleton at [6,6] ring junction and form a fused aziridine ring;
- F is a fullerene core;
- Z is selected from the group consisting of —CO$_2$H, —SO$_3$H and —PO$_3$H; and
- m is 1–10.

The preparation of the compounds of Formula II has been disclosed in Shiu, L. L., et al., *J. Chem. Soc. Perkin Trans.* 1:3355–3357, which is incorporated herein by reference.

According to an embodiment of the invention, the water-soluble fullerene derivatives include pharmaceutically acceptable salts thereof, which can be prepared using conventional techniques known to those skilled in the art.

In another embodiment of the invention, the water-soluble fullerene derivative is of the Formula I wherein
- X and Y are independently —CO$_2$H;
- n is 1; and
- m is 3.

The substituents in the water soluble fullerene derivative in Formulas I and II are distributed on the fullerene skeleton at different positions when m is 2–10.

Persons skilled in the art can appreciate that the water soluble fullerene derivatives can form a mixture of water-soluble fullerene derivatives for use in the invention.

One skilled in the art will appreciate that suitable methods of administering water soluble fullerene derivative compositions of the present invention to an animal, such as a mammal, are available, and, although more than one route can be used to administer a particular composition, a particular route can provide a more immediate and more effective reaction than another route. Pharmaceutically acceptable carriers are also well-known to those who are skilled in the art. The choice of carrier will be determined, in part, both by the particular composition and by the particular method used to administer the composition. Accordingly, there is a wide variety of suitable formulations of the pharmaceutical compositions of the present invention.

Suitable specific forms of administration include the forms for the oral route, buccal and sublingual forms of administration, subcutaneous, transdermal, intramuscular or intravenous forms of administration and rectal forms of administration, as well as forms for inhalation. For topical application, the compounds according to the invention may be used in creams, ointments or lotions.

In the pharmaceutical compositions of the present invention for oral, buccal, nasal, sublingual, subcutaneous, intramuscular, intraperitoneal, intracranial, intravenous, topical, transdermal or rectal administration, water soluble fullerene derivatives may be administered in sustained or controlled release forms or in dosage unit forms of administration mixed with standard pharmaceutical vehicles to animals or humans. The formulations may conveniently be prepared by any of the methods well known in the art.

Formulations suitable for oral administration can consist of: (a) liquid solutions or elixirs, such as an effective amount of the water soluble fullerene derivatives dissolved in diluents, such as water, alcohol, oil, or saline, or other excipients; (b) capsules, tablets, pills, powders, or lozenges each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

The formulations can additionally include: lubricating agents such as talc, magnesium stearate, and mineral oil; wetting agents; emulsifying and suspending agents; preserving agents such as methyl- and propylhydroxybenzoates; sweetening agents; and favoring agents. The compositions of the invention can be formulated so as to provide quick, sustained or delayed release of the active ingredient after administration to the patient by employing procedures known in the art.

Water soluble fullerene derivatives can be made into aerosol formulations to be administered via inhalation. Compositions for inhalation include solutions and suspensions in pharmaceutically acceptable, aqueous or organic solvents, or mixtures thereof, and powders. The liquid or solid compositions may contain pharmaceutically acceptable excipients. The compositions may be administered by an oral or nasal respiratory route for local or systemic effect. Pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

Formulations suitable for parenteral administration include aqueous and non-aqueous solutions, isotonic sterile injection solutions, which can contain anti-oxidants, buffers such as acetate and phosphate, toxicity adjusting agents, such as sodium chloride, pH adjusting agents, such as hydrochloric and phosphoric acid, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The water soluble fullerene derivative compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

For preparing solid compositions such as tablets, the principal active ingredient is mixed with a pharmaceutical excipient to form a solid preformulation composition containing a homogeneous mixture of a compound in the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above.

The tablets or pills of the present invention may be coated or otherwise compounded to provide a dosage form affording the advantage of prolonged action. For example, the tablet or pill can comprise an inner dosage and another dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, including a number of polymeric acids and mixtures of polymeric acids, such as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like. The size of the dose also will be determined by the existence, nature, and extent of any adverse side-effects that might accompany the administration of a particular composition. A suitable dose for intraperitoneal administration is about 10 to about 100 mg/kg per day.

The water soluble fullerene derivatives may be administered concurrently with other necessary medications. For example, one or more antibacterial, antiviral or antiinflammatory medications may be administered before, concurrently and after treatment with the water soluble fullerene derivatives.

Although the examples of the present invention involve the treatment of disorders associated with bacterial or viral infection in mice, particularly of the bacterial meningitis type, the methods of the present invention may be used to treat these disorders in humans and animals of any kind. Examples of suitable animals, include but are not limited to dogs, pigs, sheep, horses, cows, cats, zoo animals, and other commercially bred farm animals.

The following examples illustrate various aspects of the present invention but are not intended to limit the scope of the claims herein.

EXAMPLES

Materials and Methods

Mice

Breeder mice of the strain B6 were purchased from the Jackson Laboratory (Bar Harbor, Mass.) or Charles River Japan, Inc. (Atsugi, Japan). There were maintained on standard laboratory chow and water ad libitum in the animal facility of the Medical College, National Cheng Kung University, Tainan, Taiwan. The animals were raised and cared for by following the guidelines set up by the National Science Counsel of the Republic of China. Eight- to 12-week-old female mice were used in all experiments.

Water-Soluble Fullerene Derivatives

A water-soluble carboxylic acid of fullerene derivative with C3 symmetry [$C_{60}(C_3)$] was synthesized as described in Dugan, L. L., et al., *Proc. Natl. Acad. Sci. USA* 94:9434–9439. The $C_{60}(C_3)$ is the water-soluble fullerene derivative is of the Formula I wherein X and Y are independently —$CO_2H$; n is 1; and m is 3; which is an effective free-radical scavenger. In the following tests, $C_{60}(C_3)$ was dissolved in phosphate-buffered saline (PBS; 2 mg/ml). The mice were given 40 mg/kg of body weight doses by intraperitoneal injection (i.p.) three times at 24, 48, and 72 hours, which was far below the lethal dose (LD). The $LD_{50}$s by intraperitoneal (i.p.) injection in rats and mice are approximately 600 and 1,000 mg/kg of body weight, respectively (Chen, H. H., et al., *Toxicol, Pathol.* 26 and 143–161 and Useng, T. H., et al., *Toxicol. Lett.* 93:29–37).

Induction of Bacterial Meningitis

A general procedure was conducted as follows:

*E. coli* ATCC 10536 was cultured in Luria-Bertain (LB) broth (1% NaCl, 1% tryptone, 0.5% yeast extract) for 12 hours and was subcultured in fresh medium for another 3 h. The concentration of *E. coli* was determined with a spectrophotometer (Beckman Instrument, Somerset, N.J.), with an optical density at 600 nm of 1 equal to 108 CFU/ml (Wang, S. D., et al., *J. Immunol.* 152:5014–5021). For the induction of meningitis, groups of three to four mice were given intracerebral injections directly into the temporal area of a volume of $5 \times 10^5$ *E. coli* cells diluted in saline. The 100% lethal dose (LD100) by intracerebral injection in B6 mice is $5 \times 10^5$ *E. coli* cells. The animals were observed every 12 hours for a total of 6 days. In some experiments, the brains were aseptically removed and were homogenized with 3% gelatin (Difco Laboratories, Detroit, Mich.) in PBS. The samples were serial diluted, poured in agar plates, and incubated at 37° C. overnight. The number of colony forming units (CFU) of E. coli was quantitated and was expressed as the mean±standard deviation per mouse. E. coli was also cultured with various concentrations of $C_{60}(C_3)$ in LB broth. The growth curve of E. coli was determined in LB broth to evaluate the direct antimicrobial activity of $C_{60}(C_3)$.

Immunohistochemistry

Groups of three to four mice were sacrificed by perfusion via cardiac puncture with PBS. The brains were removed and embedded in OCT compound (Miles Inc., Elkhart, Ind.) and were then frozen in liquid nitrogen. Four-micrometer cryosections were made and were fixed with ice-cold acetone for 3 min. They were then stained with a primary rat anti-TNF-alpha monoclonal antibody (MAb; MAb MP6-XT3; PharMingen, San Diego, Calif.) or a hamster anti-IL-1-beta MAb (Genzyme, Cambridge, Mass.). Secondary antibodies were peroxidase-conjugated sheep anti-rat immunoglobulin G (IgG), goat anti-hamster IgG, or swine anti-goat IgG (Boehringer Mannheim GmbH, Mannheim, Germany). A peroxidase stain with a reddish brown color was developed with an aminoethyl carbazole substrate kit (ZYMED Laboratories, San Francisco, Calif.) (Ho, T. S., et al., J. Biomed. Sci. 4:300–307).

Detection Of Increased Vasopermeability Of BBB By M4 Tracer With Beta-Galactosidase Activity An E. coli mutant (mutant M4) that constitutively expresses beta-galactosidase was used as the tracer to detect alterations in the vasopermeability of the BBB. M4 was selected from E. coli K-12 that grew in an M63 culture plate (0.3% $KH_2PO_4$, 0.7% $K_2HPO_4$, 0.2% $(NH_4)_2SO_4$, 0.1 mM $FeSO_4$I containing 0.2% lactose, 0.002% vitamin B1, 1 mM $MgSO_4$, 0.001% isoleucineleucine-valine, and 0.002% 5-bromo-4-chloro-3-indolyl-beta-D-galactopyranoside (X-Gal)). The M4 mutant constitutively expresses beta-galactosidase and has a characteristic blue colony on medium containing X-Gal without induction. Preliminary studies have demonstrated that M4 is avirulent (LD50>2× 109 cells) to mice and that M4 was rapidly removed from the circulation. It can be used as an inert tracer within 10 min after injection. To each mouse into which E. coli was injected, $2 \times 10^8$ cells of the M4 tracer in 0.1 ml were given intravenously 2 min before the mice were killed. The brains were removed, cryosectioned, and fixed in 0.2% glutaraldehyde (Merck GmbH, Parmstadt, Germany). The M4 in the tissues was detected by X-Gal staining (1 mg of X-Gal per ml in 20 mM potassium ferricyanide, 20 mM potassium ferrocyanide, and 2 mM magnesium chloride) at 37° C. for 2 hours.

Test Protocols for Anti-bacterial Activity

Test 1

Groups of 10 B6 mice were inoculated intracerebrally with $5 \times 10^5$ E. coli per mouse. Various doses (10, 20, 30 and 40 mg/kg) of $C_{60}(C_3)$ were administrated i.p. immediately before E. coli injection. Dexamethasone (6 mg/kg of body weight given i.p.) was used as a control treatment. The reagents were given again at 24 and 48 hours. The mice were monitored for death every 12 hours for 6 days. The results are provided in FIG. 1.

Test 2

Figure 2:
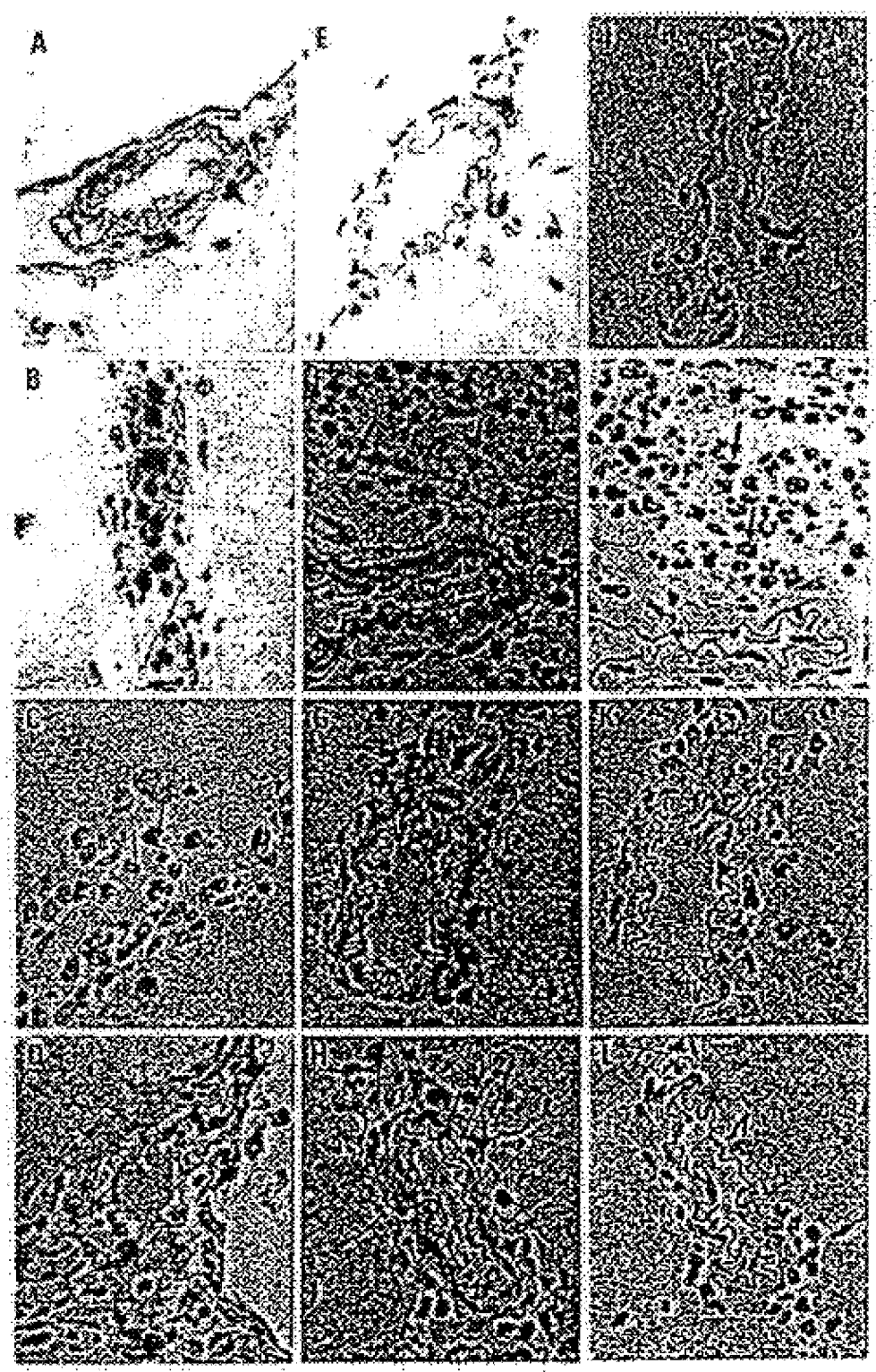
FIG. 2 is a series of photomicrographs illustrating the histological effects of $C_{60}(C_3)$ on the brain inflammation induced by E. coli in B6 mice.

FIG. 2 illustrates the data supporting that $C_{60}(C_3)$ treatment inhibited the brain inflammation induced by E. coli-injected B6 mice.

Groups of three B6 mice were inoculated intracerebrally with $5 \times 10^5$ E. coli cells per mouse, and the mice were killed at 24 hours postinjection.

$C_{60}(C_3)$ (40 mg/kg per mouse) was administered i.p. immediately before E. coli injection. $C_{60}(C_3)$ (40 mg/kg per mouse) was administered i.p. 6 hours after E. coli injection. The M4 tracer ($2 \times 10^8$ cells in 0.1 ml) was injected intravenously 2 min before the mice were killed. The results are shown in FIG. 2. Four-micrometer cryosections of frozen brain tissues were stained with X-Gal (A to D) or anti-TNF-alpha (E to H) and anti-IL-1 (I to L), as described in Materials and Methods.

Test 3

Figure 3:
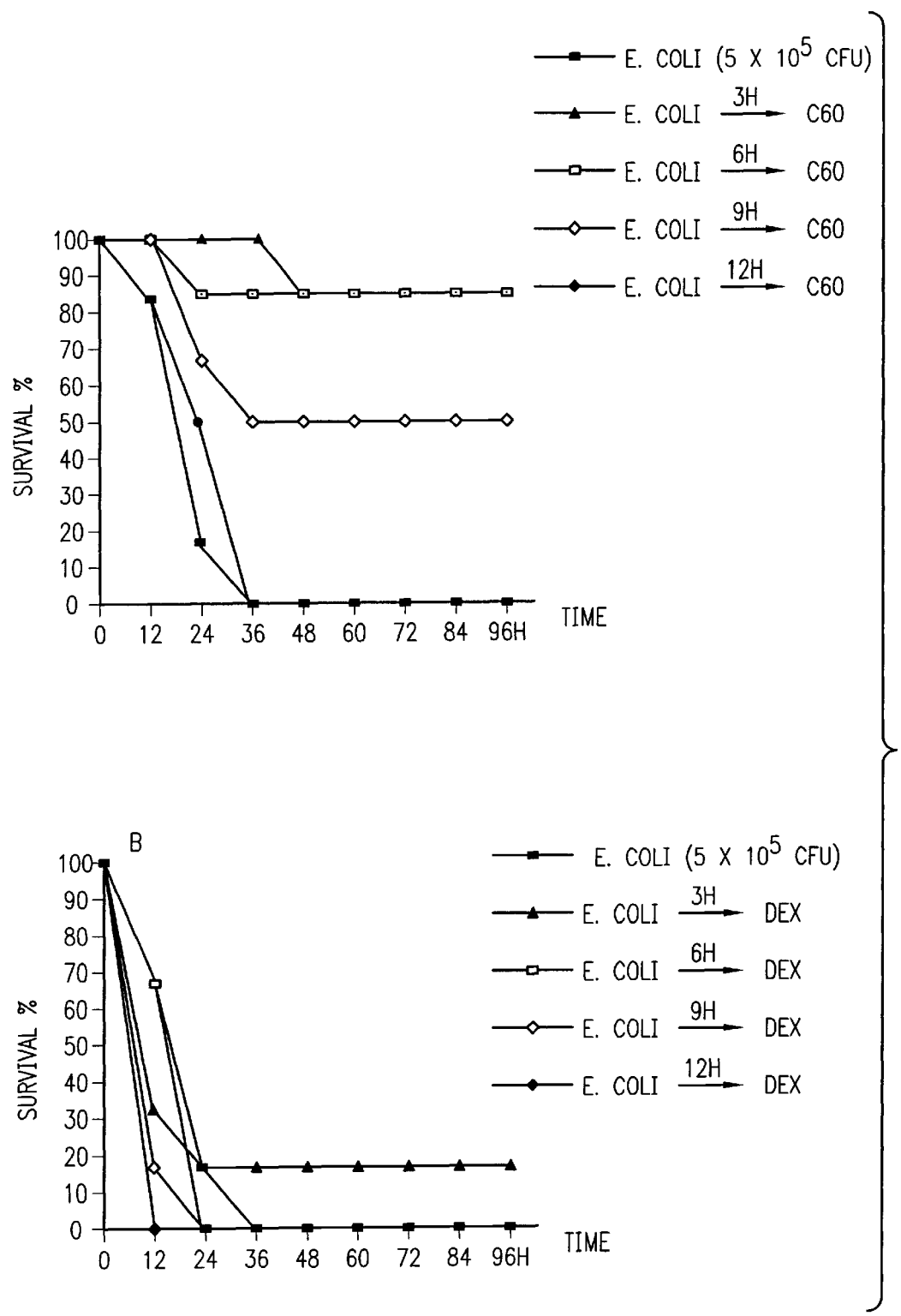
FIG. 3 are graphs showing the therapeutic effect of $C_{60}(C_3)$ on E. coli-induced death in B6 mice and the therapeutic effects of dexamethasone on E. coli-induced death in B6 mice as a control for the experiment run with $C_{60}(C_3)$.

FIG. 3 relates to the therapeutic effect of $C_{60}(C_3)$ on E. coli-induced death in B6 mice. Groups of six B6 mice were inoculated intracerebrally with $5 \times 10_5$ E. coli cells per mouse. $C_{60}(C_3)$ (40 mg/kg per mouse) was administered i.p. at various times after E. coli injection. Dexamethasone (5 mg/kg of body weight given i.p.) was used as a control treatment. The reagents were given against again at 24 and 48 hours. The mice were monitored for death every 12 hours for 6 days.

Test 4

Figure 4:
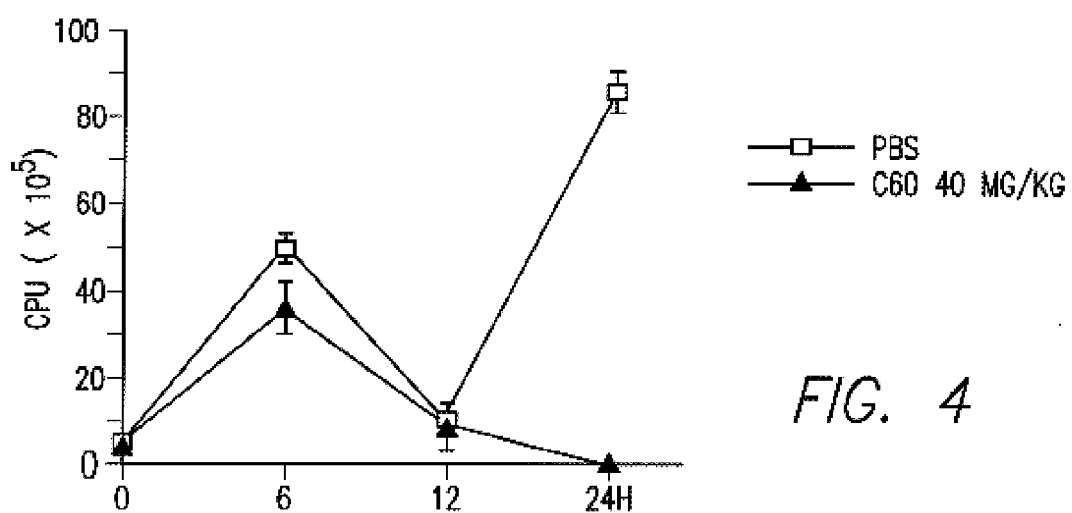
FIG. 4 is a graph showing the effects of $C_{60}(C_3)$ on the in vivo growth of E. coli.

In vitro and in vivo tests were conducted to determine the amount of E. coli growth. E. coli ($4 \times 10^6$/ml cells) was cultured with various concentrations of $C_{60}(C_3)$ in LB broth, and the growth curve was determined with a spectrophotometer. FIG. 4 relates to the effect of $C_{60}(C_3)$ on the in vivo growth of E. coli.

In vivo, groups of three mice were given intracerebral injections of $5 \times 10^5$ E. coli cells. $C_{60}(C_3)$ (40 mg/kg per mouse) was administered i.p. before E. coli injection. At various times (at 6, 12, 24 hr) postinoculation, postinjection, the brains were aseptically removed and homogenized, and the numbers of CFU of E. coli were quantitated in an agar plate and are expressed as the mean±standard deviation per mouse. The results are shown in FIG. 4.

Test 5

Figure 5:
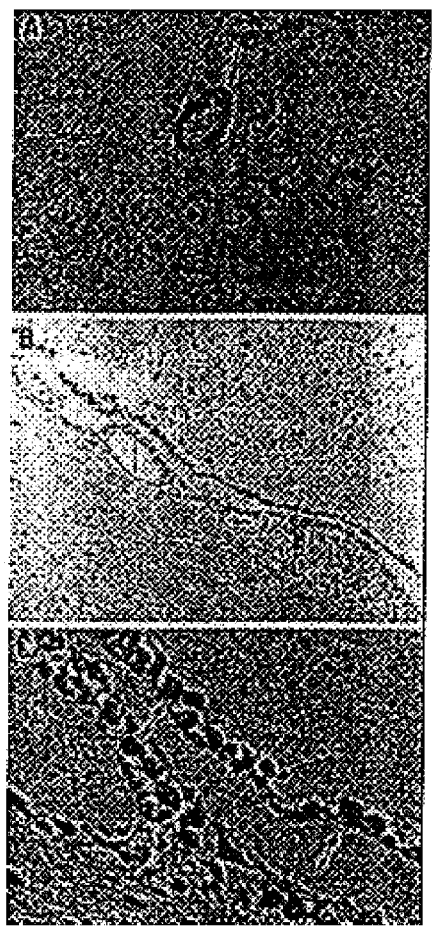
FIG. 5 is a series of photomicrographs showing the histological effects of $C_{60}(C_3)$ on the induced TNF-alpha expression in the brain.

FIG. 5 relates to $C_{60}(C_3)$ treatment which induced TNF-alpha expression in the brain.

Groups of three B6 mice were inoculated i.p. with $C_{60}(C_3)$ (40 mg/kg per mouse) and were killed at 24 hours postinjection. Four-micrometer cryosections of frozen brain tissues were stained with anti-TNF-alpha) (40 mg/kg per mouse) and were sacrificed at 24 hours postinjection. Four-micrometer cryosections of frozen brain tissues were stained with anti-TNF in the amount of 40 mg/kg per mouse and were sacrificed at 24 hours postinjection. Four micrometer cryosections of frozen brain tissues were stained with anti-TNF-alpha as described in Materials and Methods.

Test 6

Gram-positive bacteria such as Staphylococcus aureus, Group A Streptococcus, Group B Streptococcus, or vancomycin-resistant Enterococcus were grown in BHI or TSBY broth. Concentrations in the amount of 5, 50, 200 microg/ml of $C_{60}(C_3)$ were added into the culture. The bacterial numbers at various times were determined by agar plates. The growth curve was expressed by CFU's per ml culture.

Test Protocol For Anti-Viral Activity

Plaque Reduction Neutralization Test

Figure 7:
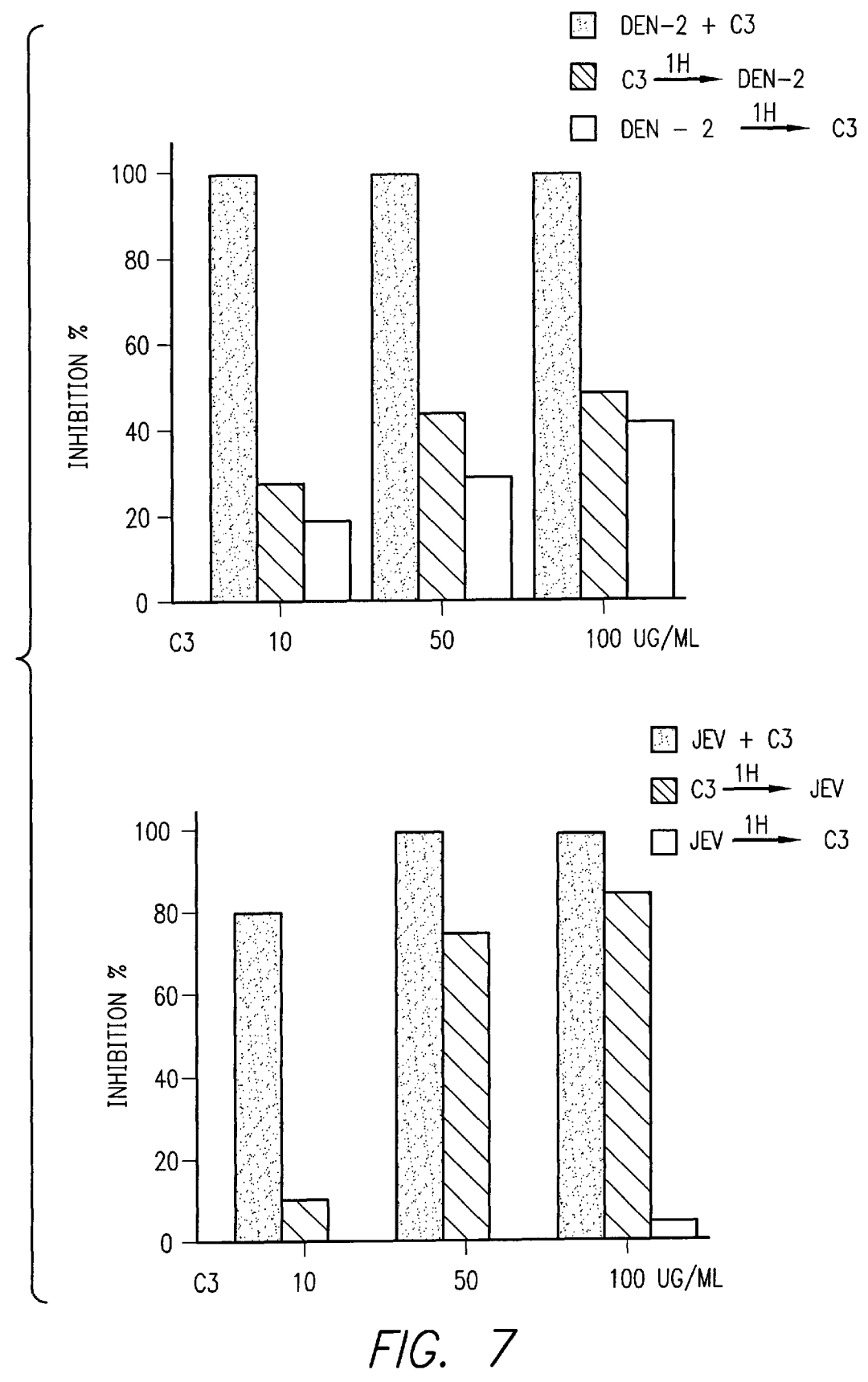

In the treatment experiments, the BHK cells were incubated with either dengue 2 virus or Japanese encephalitis virus ($10^3$ to $10^4$ plaque forming units (PFU)). The $C_{60}(C_3)$ in the amount of 10, 50, or 100 μg/ml was added at the beginning of incubation. At the end of 5-day incubation, PFU was determined. In the pre-treatment experiments, the BHK cells were treated with $C_{60}(C_3)$ for 1 hr followed by washing to remove $C_{60}$. The BHK cells were then infected with either dengue 2 virus or Japanese encephalitis virus ($10_3$ to $10_4$ PFU) and incubated for 5 days. In the post-treatment experiments, the BHK cells were infected with the virus for 1 hour followed by washing to remove the virus. The $C_{60}$ was added to the BHK cells, then incubated for 5 days. The percentage of inhibition was calculated by comparing to a control group. The results are shown in FIG. 7.

Results

Inhibition of Experimental E. coli-induced Meningitis by $C_{60}(C_3)$

Intracerebral injection of E. coli in B6 mice induced TNF-alpha and IL-1-beta production in the brain and recruited neutrophil infiltration into the brain at 6 to 9 hours postinjection. Without treatment the mice will die within 36 hours of intracerebral injection of $2\times10^5$ E. coli cells (the LD100 for mice). However, treatment of each mouse with 40 mg of $C_{60}(C_3)$ per kg i.p. protected the mouse from E. coli-induced death. The inhibition was dose-dependent; 20 mg of $C_{60}(C_3)$ per kg protected 40% of the mice, while 30 mg/kg protected 75% of the mice. This inhibitory effect was better than that of dexamethasone (6 mg/kg), which protected only 20% of the mice.

As shown, the increased vasopermeability of the BBB detected with the M4 tracer was manifested at 24 hours in E. coli-treated mice. However, in the $C_{60}(C_3)$-treated mice, these increases in BBB permeability were inhibited. Furthermore, the TNF-alpha and IL-1-beta staining intensities on arterioles or infiltrating neutrophils were lower in $C_{60}(C_3)$treated mice than in nontreated mice. This is consistent with the observation that less neutrophil infiltration occurs in $C_{60}(C_3)$-treated mice. Apparently, the $C_{60}(C_3)$ treatment decreases the level of cytokine production in the brain, which consequently inhibits the increase in BBB permeability and protects the mice from E. coli-induced death.

Therapeutic Effect of $C_{60}(C_3)$ on E. coli-induced Meningitis in B6 mice

As shown in FIG. 3, the mice died within 36 hours after the injection of $5\times10^5$ E. coli cells. In contrast, intraperitoneal administration of 40 mg of $C_{60}(C_3)$ per kg as late as 6 hours after E. coli injection protected 80% of the mice from E. coli-induced death. There was still a 50% survival rate if $C_{60}(C_3)$ was given at 9 hours postinfection. Dexamethasone is used clinically, and it primarily inhibits cytokine production. However, it can only delay or partially inhibit the experimental E. coli-induced death. The protective effect of $C_{60}(C_3)$ was better than that of dexamethasone, which had only a preventive effect (FIG. 3). The cytokine expression, increase in BBB permeability, and neutrophil infiltration were also inhibited in the groups treated with $C_{60}(C_3)$ delayed injection.

Immunomodulatory Effect of $C_{60}(C_3)$ in the Brain

The growth of E. coli in the brain after intracerebral injection was determined after $C_{60}(C_3)$ treatment. As shown in FIG. 4, the number of E. coli cells in the brain was not lower in $C_{60}(C_3)$-treated mice than in nontreated mice 12 hours after intracerebral injection of E. coli. However, the E. coli cells were cleared from the brain after 24 hours in $C_{60}(C_3)$-treated mice, while they replicated significantly in nontreated mice, suggesting that $C_{60}(C_3)$ enhanced the natural antibacterial defenses in the brain. This is supported by the observation that TNF-alpha expression was found in brain endothelial cells or ependymal cells from mice treated with $C_{60}(C_3)$ alone. Given the above, a water-soluble malonic acid derivative of $C_{60}(C_3)$ could interfere with the inflammatory response in experimental E. coli-induced meningitis. $C_{60}(C_3)$ not only suppressed cytokine production as well as increased permeability of the BBB, but it also inhibited neutrophil infiltration into the brain. $C_{60}(C_3)$ can also modulate the natural antibacterial defense in the brain. Furthermore, $C_{60}(C_3)$ is still effective 9 hours after E. coli injection, indicating that it can interfere with neutrophil activation.

Given the above, $C_{60}(C_3)$ modulates the natural antibacterial defense to clear the bacteria from the brain. Since the proinflammatory cytokines induced in meningitis interact in a complex cascade, no single intervention is effective. $C_{60}(C_3)$ can thus be used as a therapeutic agent for bacterial meningitis.

Antibacterial Effect

Figure 6:
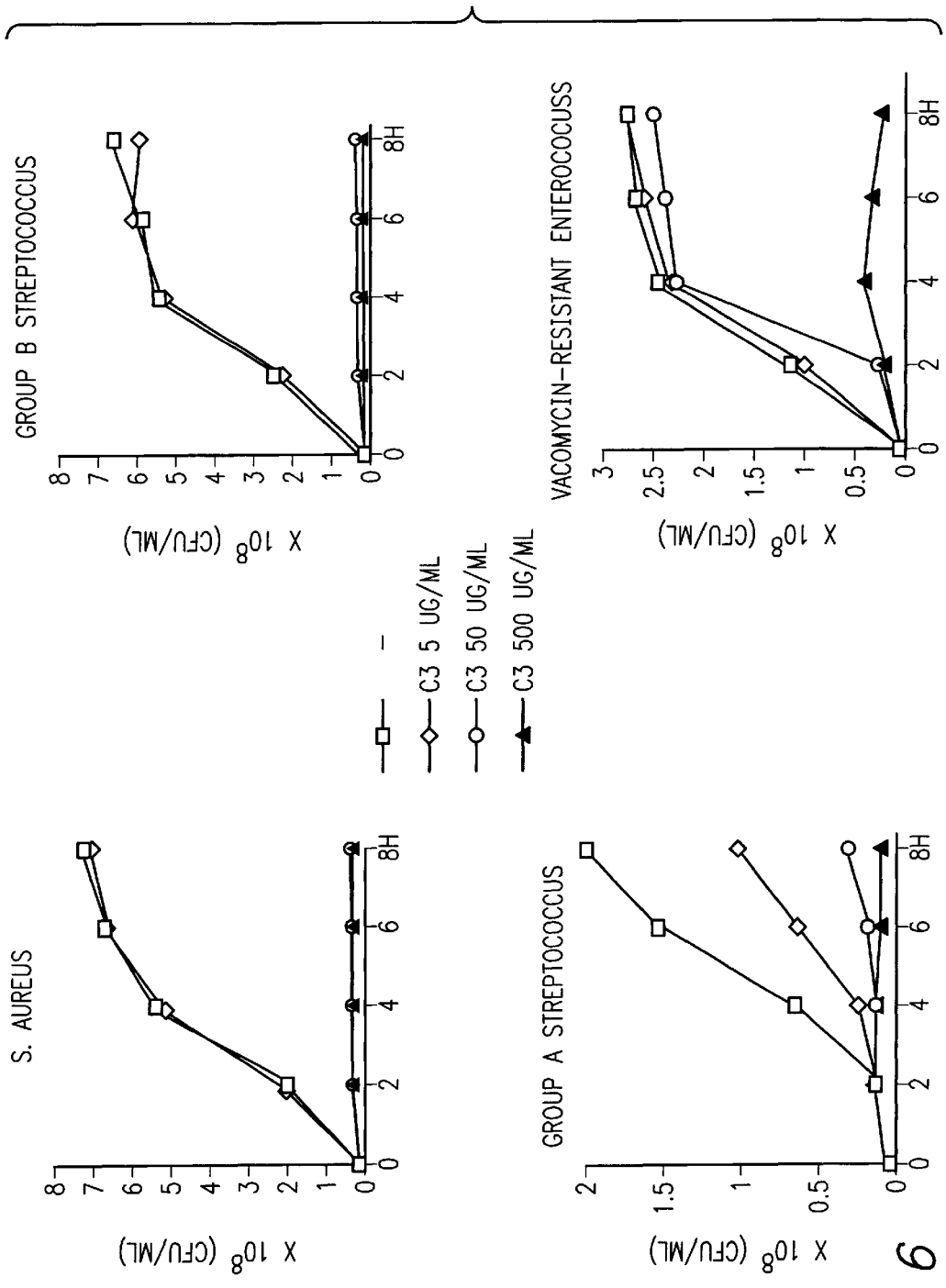
FIG. 6 are graphs showing the effects of $C_{60}(C_3)$ on Gram-positive bacteria.

As demonstrated in FIG. 6, $C_{60}(C_3)$ can significantly decrease CFU number of S. aureus, Streptococcus, and Enterococcus. $C_{60}(C_3)$ is useful as an inhibitor for bacterial infection.

Antiviral Effect

As illustrated in FIG. 7, $C_{60}(C_3)$ has an inhibitory effect on the growth of dengue 2 virus and Japanese encephalitis virus. $C_{60}(C_3)$ can be used as a therapeutic agent for viral infection.

Group A Streptococcus-Induced Death

Figure 8:
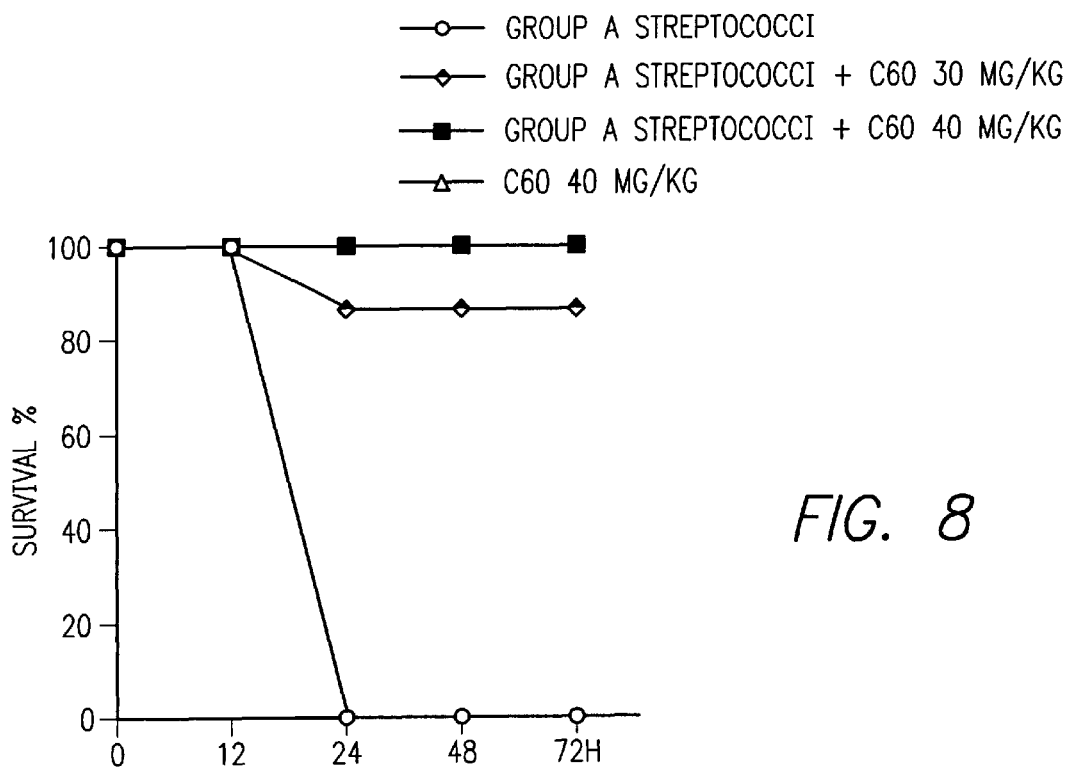
FIG. 8 is a graph showing the effect of fullerene on Group A Streptococci infected mice.

In yet another experiment, groups of eight B6 mice were infected by direct injection into the air pouch of $2\times10^8$ group A Streptococci in 0.1 ml of fluid per mouse. The air pouch was formed by injecting about 1 ml of air into the back of the mouse subcutaneously three times for three successive days before Streptococci injection. Various doses of $C_{60}$ were administered before Group A Streptococci injections. The reagents were given at 24 hours and 48 hours. Mouse mortality was measured every 24 hours for 6 days. The results indicate that administration of $C_{60}$ increased mouse survival. Notably, without the administration of the fullerene, mortality occurred within 24 hours of Streptococci injection. By altering the concentration of fullerene administered, it is shown that survival rates increased (FIG. 8).

Neutrophil Infiltration Enhancement

Figure 9:
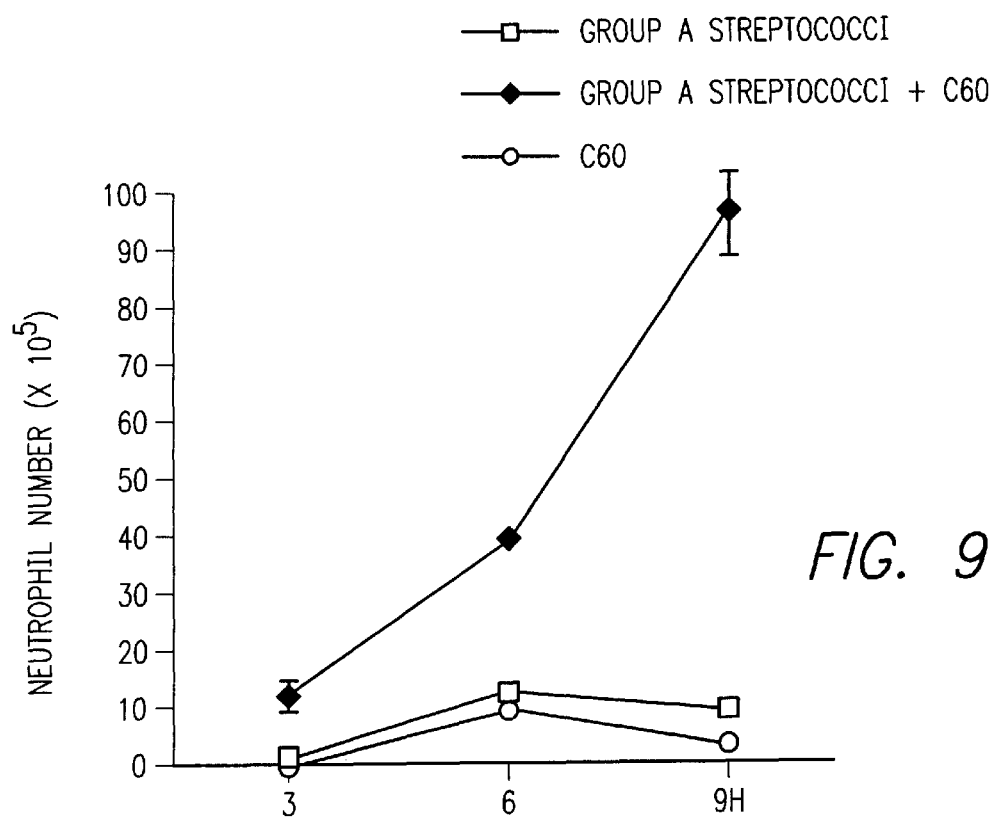
FIG. 9 is a graph showing neutrophil infiltration after Group A Streptococci infection.

In yet another experiment, groups of four B6 mice were infected by direct injection of $2\times10^8$ Group A Streptococci in about 0.1 ml per mouse, into the air pouch. The fullerene was injected at about 40 mg/kg body weight into the pouch together with the streptococci. The infiltrating cells in the pouch were collected by injecting about 1 ml of phosphate buffer saline into the pouch and aspirating the exudates. The total viable cell counts were made at 3, 6, and 9 hours after infection. The results indicated that fullerenes in combination with the Streptococci showed a remarkable increase of neutrophil infiltration, notably at the 9-hour mark (FIG. 9).

Neutrophil Longevity Enhancement

Figures 10, 11:
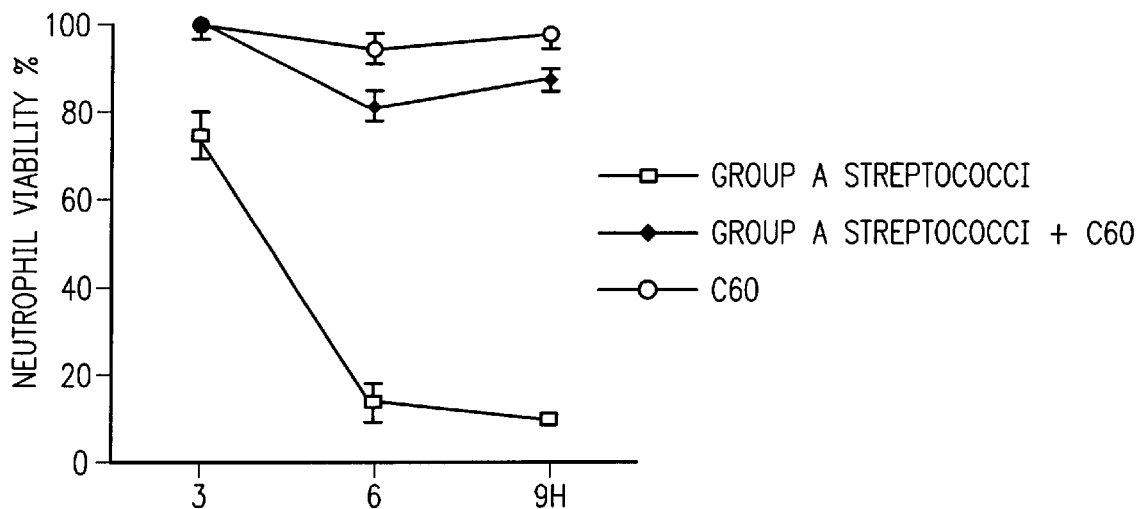
FIG. 10 is a graph showing neutrophil viability after Group A Streptococci infection.
FIG. 11 is a table demonstrating bactericidal activity by neutrophils.

In yet another experiment, groups of eight B6 mice were infected by direct injection of $2\times10^8$ Group A streptococci per mouse, into the air pouch. Fullerenes at 40 mg/kg body weight were injected into the pouch together with the streptococci. The infiltrating cells in the air pouch were collected by injecting 1 ml of phospate buffer saline into the pouch and aspirating the exudates. The viable cell count was obtained at 3, 6, and 9 hours. The results indicated that fullerenes enhance the viability of infiltrating neutrophils (FIG. 10).

Neutrophil Bactericidal Activity Enhancement

Neutrophils were isolated from the peripheral blood system by Ficoll-paque centrifugation. Neutrophils ($1\times10^6$ in 1 ml) were incubated with various doses of fullerenes for 4 hours. After washing with phosphate buffer, the neutrophils were incubated with Group A Streptococci ($2\times10^8$) for 1 hour. The numbers of survival streptococci were determined on blood agar plates. The results indicated that increasing concentrations of fullerenes caused an increase in bactericidal activity by the neutrophils (FIG. 11).

Inhibition of Disease After Fullerene Treatment

Figure 12:
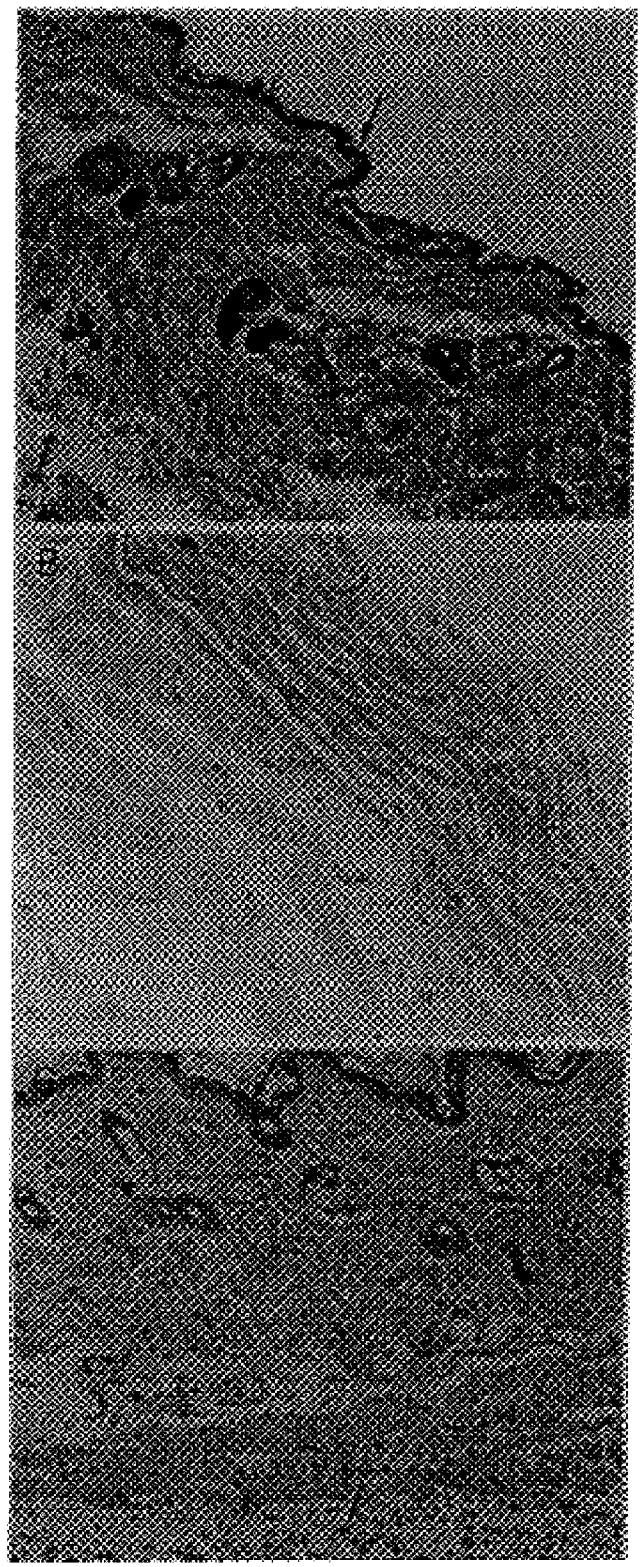
FIG. 12 is a series of photomicrographs illustrating that fullerene reduces tissue damage caused by Group A Streptococci infection.

In yet another experiment, groups of three B6 mice were infected by direct injection of $2\times10^8$ Group A Streptococci per mouse, into the air pouch. Fullerenes, such as $C_{60}$ at a concentration of 40 mg/kg of body weight were administered prior to streptococci injection. The mice were sacrificed at 24 hours and the tissues around the pouch were excised and histologically prepared. Histology indicated that skin damage was reduced after $C_{60}$ treatment. See FIG. 12.

Inhibition of Tumor Necrosis Factor (TNF-alpha) in Bacterial Meningitis

It is known that *E. coli*-induced meningitis is fatal. Upon infection, cytokine production, such as TNF-alpha and interleukins, increases. Accordingly, the blood brain barrier (BBB) becomes more permeable, thus allowing the traditional immune responses to occur within the nervous system. However, the increased permeability permits neutrophils and plasma proteins to permeate into the nervous system and thereby cause further damage. Accordingly, fullerenes were used to inhibit cytokine production. In this experiment, groups of three B6 mice were infected by direct injection of $5\times10^9$ Group A streptococci per mouse, into the air pouch. Fullerenes, such as $C_{60}$ at a concentration of 40 mg/kg of body weight were injected prior to the streptococci injection. The mice were sacrificed at 24 hours with the skin tissue excised and prepared histologically by staining with anti-TNF or anti-IL-6. In other experiments, the dosages were varied to maximize viability. For example, various doses from 20 mg/kg to 40 mg/kg were injected. It should be noted, however, that any effective amount may be utilized so as to provide therapeutic benefits without untoward toxicity (i.e., from about 0.001 mg/kg to about 100 mg/kg).

Figure 13:
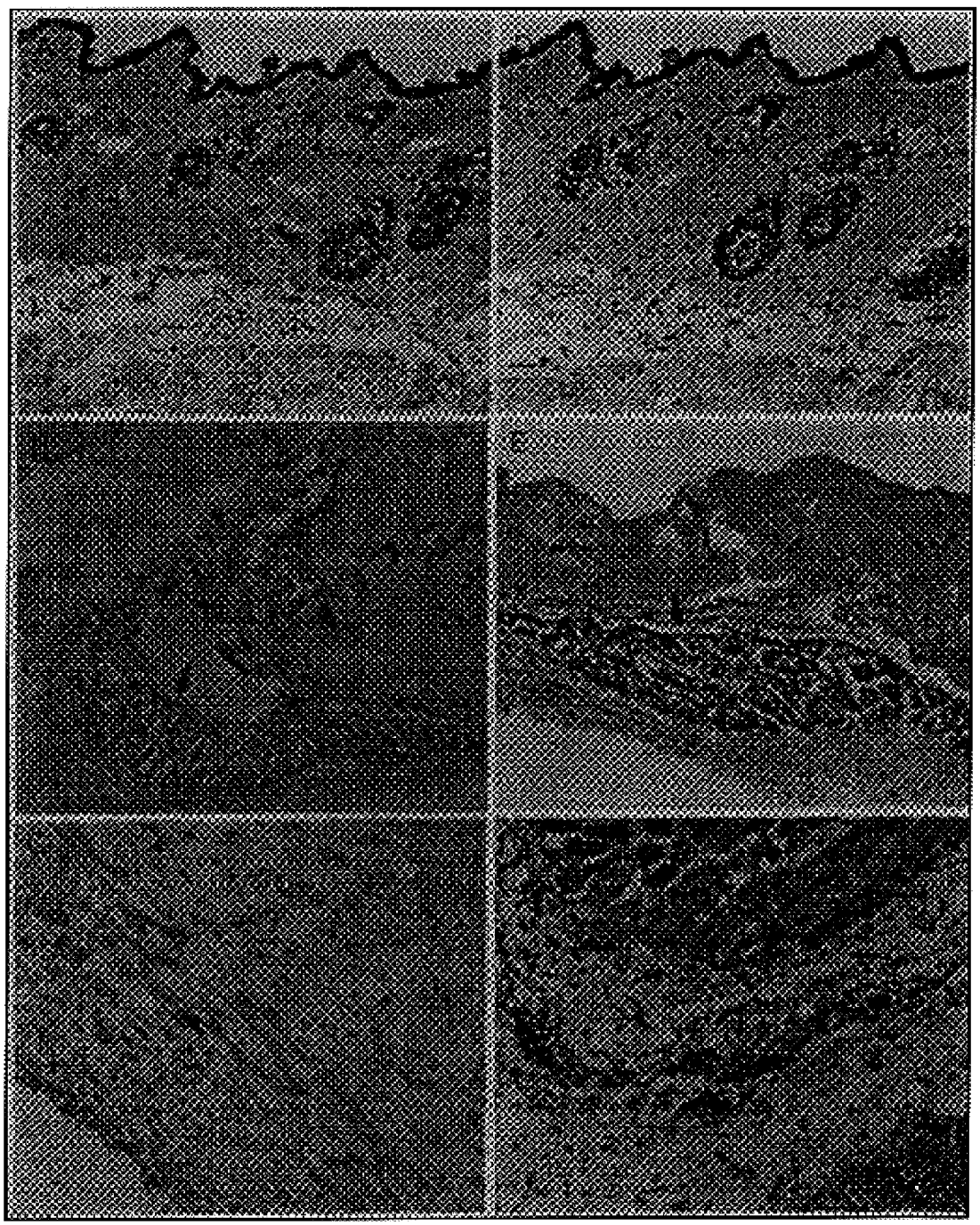
FIG. 13 is a series of photomicrographs demonstrating that fullerene therapy reduces TNF and IL expression.

The results demonstrate that treatment employing the 40 mg/kg dose protected the mouse from *E. coli*-induced meningitis. In other doses, a 20 mg/kg dose protected 40% of the mice; whereas a 30 mg/kg dose protected 75% of the mice. This was unexpected given that dexamethasone at a concentration of 6 mg/kg protected only 20% of the mice. Histological preparations indicated that permeability decreased with fullerene administration. Accordingly, there was less neutrophil and protein seepage across the barrier and consequently, mortality decreased. The fullerene, therefore, acted to decrease the level of cytokine production in the brain. Furthermore, injection of fullerenes after several hours of meningeal infection still resulted in decreased mortality. For example, when 40 mg/kg of fullerenes ($C_{60}$) were injected 6 hours after meningeal infection, the fullerene administration protected about 80% of the mice. Similarly, when the fullerene administration occurred 9 hours post-meningeal infection, about 50% of the mice survived. See FIG. 13.

Although the invention has been described with respect to specific embodiments, it should be appreciated that other embodiments utilizing the concept of the present invention are possible without departing from the scope of the invention. The invention, for example, is not intended to be limited to the specific doses and dosage forms exemplified and disclosed in these embodiments; rather the invention is defined by the claimed elements and the equivalents thereof.

We claim:

1. A method for treating a disease, comprising administering to a subject a therapeutically effective amount of a pharmaceutical composition comprising a compound of Formula II:

wherein
  N is attached to two vicinal carbon atoms of a fullerene skeleton at a [6,6] ring junction and form a fused aziridine ring;
  F is a fullerene core;
  Z is selected from the group consisting of —$CO_2H$, —$SO_3H$ and —$PO_3H$; and
  m is 1—10;
  or a pharmaceutically acceptable salt thereof.

2. The method of claim 1, wherein the pharmaceutical composition further comprises a pharmaceutically acceptable carrier.

3. The method of claim 1, wherein the disease is selected from a group consisting of a bacterial disease and a viral disease.

4. The method of claim 3, wherein the viral disease is that caused by a virus selected from a group consisting of Dengue 2 and encephalitis virus.

5. The method of claim 3, wherein the bacterial disease is that caused by a bacterium selected from a group consisting of Gram positive and Gram negative bacterium.

6. The method of claim 1, wherein the amount administered is from about 0.001 to about 100 mg/kg of body weight of the subject.

7. The method of claim 1, wherein the amount administered is from about 20 to about 40 mg/kg of body weight of the subject.

8. The method of claim 1, wherein the disease comprises an infection by at least one of a *E. coli, Staphylococcus aureus*, Group A streptococcus, Group B streptococcus, or vancomycin-resistant Enterococcus bacterium.

9. A method for treating a bacterial or viral disease comprising administering to a subject a therapeutically effective amount of a pharmaceutical composition comprising a compound of Formula I:

wherein
  C is attached to two vicinal carbon atoms of a fullerene skeleton at a [6,6] ring junction and form a fused cyclopropane ring;

F is a fullerene core;

X and Y are identical or different, and are independently selected from the group consisting of —$CO_2H$, —$SO_3H$ and —$PO_3H$;

n is 0 or 1; and m is 1–10;

or a pharmaceutically acceptable salt thereof.

10. The method of claim 9, wherein

X and Y are independently —$CO_2H$;

n is 1; and m is 3.

11. The method of claim 9, wherein C, X and Y are distributed on the fullerene skeleton at different positions when m is 2–10.

12. A method for inhibiting cytokine production, comprising administering to a subject a pharmaceutically effective amount of a pharmaceutical composition comprising a fullerene.

13. The method of claim 12, wherein the cytokine is selected from a group consisting of tumor necrosis factor-alpha and interleukin.

14. The method of claim 12, wherein the amount administered is about 0.001 to about 100 mg/kg of body weight of the subject.

15. A method for enhancing neutrophil infiltration to treat a disease, comprising administering to a subject a therapeutically effective amount of a pharmaceutical composition comprising a fullerene.

16. The method of claim 15, wherein the disease is selected from a group consisting of a bacterial disease and a viral disease.

17. The method of claim 15, wherein the amount administered is about 0.001 to about 100 mg/kg of body weight of the subject.

18. The method of claim 9, wherein the pharmaceutical composition further comprises a pharmaceutically acceptable carrier.

19. The method of claim 9, wherein the viral disease is that caused by a virus selected from a group consisting of Dengue 2 and encephalitis virus.

20. The method of claim 9, wherein the bacterial disease is that caused by a bacterium selected from a group consisting of Gram positive and Gram negative bacterium.

21. The method of claim 9, wherein the amount administered is from about 0.001 to about 100 mg/kg of body weight of the subject.

22. The method of claim 9, wherein the amount administered is from about 20 to about 40 mg/kg of body weight of the subject.

23. The method of claim 9, wherein the disease comprises an infection by at least one of a *E. coli, Staphylococcus aureus*, Group A streptococcus, Group B streptococcus, or vancomycin-resistant Enterococcus bacterium.

\* \* \* \* \*